United States Patent [19]
Hodge et al.

[11] Patent Number: 5,756,707
[45] Date of Patent: May 26, 1998

[54] METHOD OF MAKING 2'-O-ALKYL PYRIMIDINE RIBONUCLEOSIDES

[75] Inventors: Richard P. Hodge, Dracut; Nanda D. Sinha, Acton, both of Mass.

[73] Assignee: PerSeptive Biosystems, Inc., Framingham, Mass.

[21] Appl. No.: 355,544

[22] Filed: Dec. 13, 1994

[51] Int. Cl.[6] .................................................. C07H 19/10
[52] U.S. Cl. ................... 536/27.11; 536/25.3; 536/26.8; 536/28.51
[58] Field of Search .................... 536/27.11, 25.3, 536/26.8, 28.51

[56] References Cited

U.S. PATENT DOCUMENTS

| | | | |
|---|---|---|---|
| 5,214,135 | 5/1993 | Srivastava et al. | 536/26.7 |
| 7,918,362 | 7/1992 | McGee et al. | |
| 7,967,267 | 10/1992 | McGee et al. | |
| 7,968,849 | 10/1992 | McGee et al. | |

FOREIGN PATENT DOCUMENTS 9402501  2/1994  WIPO.

OTHER PUBLICATIONS

Inoue et al., "Synthesis and Properties of Novel Nucleic Acid Probes," *Thirteenth Symposium on Nucleic Acids Chemistry, Nucleic Acids Research Symposium Series*, (vol.) No. 16, IRL Press, Oxford, England, 1985, pp. 165–168.
Goodman, "Chemical Synthesis and Transformations of Nucleosides," Ch. 2 in *Basic Principles in Nucleic Acid Chemistry*, vol. 1, Ts'o (ed.), 1974 Academic Press, New York, NY, pp. 94–208, only pp. 143–146 & 201–202 supplied.
Kochetkov et al., "Reactions of the Carbohydrate Residues of Nucleic Acids," Ch. 9 in *Organic Chemistry of Nucleic Acids, Part B*, Plenum Press, New York, NY, 1972, pp. 449–476, only pp. 458–461 and 471–474 supplied.
Otsuka et al., "2'-O-Methyl RNA," *Chem. Abstr.*, 106(19), p. 726, Abstr. No. 156829v (1987); JP 61,291,595, 22 Dec. 1986; both documents supplied.
Honjo et al., "O-Methyluridines and –cytidines," *Chem Abstr.*, 70(15), p. 432, Abstr. No. 68711h (1969); JP 68 23627, 11 Oct. 1968; both documents supplied.
Hakimelahi et al., "New Catalysts and Procedures for the Dimethoxytritylation and Selective Silylation of Ribonucleosides," *Can. J. Chem.*, 60, 1106–1113 (1982).
Darzynkiewicz et al., "O'–Methyl Derivatives of Arabinosylcytosine," *Biochem. Biophys. Res. Comm.*, 46(4), 1734–1741 (1972).

Wagner et al., "Preparation and Synthetic Utility of Some Organotin Derivatives of Nucleosides," *J. Org. Chem.*, 39(1), 24–30 (1974).
Gholam H. Hakimelahi et al., *Can. J. Chem.*, (1982) 60:1106–13.
K. Yamauchi et al., *Bull Chem. Soc. JPN.*, 59:2947–49 (Sep. 1986).
Vaijayanti Kumar et al., *Bull. Chem. Soc. JPN.*, 65:1665–67 (Jun. 1992).
Beijer et al., Nucleic Acids Res., (1990) 18:5143–5151.
Broom et al., J. Am. Chem. Soc., (1965) 87:1145–1146.
Chanteloup et al., Tett. Lett., (1994) 35: 877–880.
Cotten et al., Nucleic Acids Res., (1991) 19: 2629–2635.
Furukawa et al., Chem. Pharm. Bull., (1965) 13: 1273–1278.
Goodchild, Nucleic Acids Res., (1992) 20: 4607–4612.
Haines, A.H., Tetrahedron, (1973) 29:2807–2810.
Inoue et al., Nucleic Acids Res., (1987) 15: 6131–48.
Kamimura et al., Chem. Lett., (1982) 965–968.
Kochetkov et al., "Organic Chemistry of Nucleic Acids,", Part B (1972) 381–397.
Lamond, Biochem. Soc. Trans., (1993) 21: 1–8.
Lamond et al., FEBS, (1993) 325: 123–127.
Martin et al., Biochem., Biochem., (1968) 7: 1406–1412.
Nyilas et al., Acta. Chemica Scand., (1986) B40: 826–830.
Pathak et al., Chemica. Scriptor, (1986) 26:135–139.
Robins et al., J. Org. Chem., (1974) 39: 1891–1899.
Shapiro et al., JACS., (1974) 96: 906–912.
Sproat et al., Nucleic Acids Res., (1989) 17: 3373–3386.
Sproat et al., Nucleic Acids Res., (1990) 18: 41–49.
Sproat et al., Nucleic Acids Res., (1991) 19: 733–788.
Ulman et al., Biochimica et Biophysica Acta., (1973) 294: 396–404.
Wagner et al., Nucleic Acids Res., (1991) 19: 5965–5971.
Wang et al., Biochimica et Biophysica Acta., (1982) 697: 371–377.
Welch et al., Chemica. Scand., (1983) 37: 147–150.

*Primary Examiner*—John Kight
*Assistant Examiner*—L. Eric Crane
*Attorney, Agent, or Firm*—Testa, Hurwitz & Thibeault, LLP

[57] ABSTRACT

Method for production of 2'-O-derivatized uridine and cytosine RNA synthons comprising derivatizing the 2'-hydroxyl group of a partially protected cytosine ribonucleoside to preferentially produce a partially protected 2'-O-derivatized nucleoside, which is then either (1) reacted at the 3'-hydroxyl group to produce a 2'-O-derivatized cytosine RNA synthon, or (2) reacted with a hydroxide source to produce a uridine nucleobase by deamination, thereby producing a partially protected 2'-O-derivatized uridine ribonucleoside which can be reacted at its 3'-hydroxyl group to produce a uridine RNA synthon.

20 Claims, 2 Drawing Sheets

METHOD OF MAKING 2'-O-ALKYL PYRIMIDINE RIBONUCLEOSIDES

BACKGROUND OF THE INVENTION

This invention relates to the field of nucleic acid chemistry. More specifically, this invention relates to novel methods for preparing partially protected 2'-O-derivatized pyrimidine ribonucleosides suitable for direct conversion to cytosine or uridine RNA synthons.

Interest in 2'-O-alkylated ribonucleosides has accelerated with the increasing realization that oligoribonucleotides may act as antisense and/or antiviral agents. For these applications, 2'-O-alkylated ribonucleic acids (Alk-RNAs) exhibit several advantages over native RNA. Alkylation of the 2'-hydroxyl group stabilizes the Alk-RNA oligomer during chemical synthesis and deprotection, increases nuclease resistance in vitro and enhances duplex stability upon hybridization to target sequences. See Sproat et al., Nucl. Acids Res., (1989) 17: 3373–3386, Beijer et al., Nucl. Acids Res., (1990) 18: 5143–5151, Lamond et al., FEBS, (1993) 325: 123–127 and Lamond, Biochem. Soc. Trans., (1993) 21: 1–8. Specific advantages of 2'-O-methyl modifications of synthetic RNA oligomers include inhibition of in vitro RNA processing, (See Cotten et al., Nucl. Acids Res., (1991) 19: 2629–2635) and enhanced catalytic activity of synthetic ribozymes. See Goodchild, Nucl. Acids Res., (1992) 20: 4607–4612. Given the current interest in oligoribonucleotides, for example as antisense and/or antiviral agents, there exists a need for improved methods for the synthesis of 2'-O-alkylated RNA synthons.

Methylation of the 2'-hydroxyl group of a ribonucleoside was first described by Broom and coworkers. See Broom et al., J. Am. Chem. Soc., (1965) 87: 1145–1146. According to the procedure, 2'-O-methyl adenosine was isolated in 40% yield when alkylated using diazomethane. When this general procedure was applied to cytidine by Martin and coworkers, a 20% yield of the 2'-O-alkylated ribonucleoside was obtained. See Martin et al., Biochem., (1968) 7: 1406–1412. Generally, these disclosures teach the alkylation of unprotected ribonucleosides using diazomethane. Thus, a mixture of 2' and 3'-O-alkylated products is generated because the alkylation reaction is not selective for the 2'-hydroxyl group. Consequently, the relatively small amount of desired 2'-O-alkylated ribonucleoside must be laboriously isolated from a crude mixture of products.

The diazomethane mediated alkylation of unprotected ribonucleosides was later improved by the addition of stannous chloride as a catalyst. See Robins et al., J. Org. Chem., (1974) 39: 1891–1899. The authors report a 74% yield of 2'-O-methyl cytosine, 15% yield of 3'-O-methyl cytosine and traces of N-methylated product. Others have extended the method to partially protected purine ribonucleosides. See Inoue et al., Nucl. Acids Res., (1987) 15: 6131–48 and Srivastava et al., U.S. Pat. No. 5,214,135. Generally, these disclosures teach the alkylation of unprotected or partially protected ribonucleosides using diazomethane and a stannous chloride catalyst. Surprisingly, there is selective alkylation of the 2'-hydroxyl group in the presence of an unprotected 3'-hydroxyl group. Diazomethane is limited to methylation reactions and ion exchange chromatography often is required to purify the crude products obtained. Also, diazomethane is toxic and explosive thereby creating a safety hazard especially in large scale preparation.

Silver (I) oxide mediated specific alkylation and allylation of the 2' hydroxyl group of ribonucleosides was first reported by Nyilas (See Nyilas et al., Acta. Chemica Scand., (1986) B40: 826–830.) and later by Inoue. See Inoue et al., Nucl. Acids Res. (1987) 15: 6131–6148. Generally, these disclosures teach the 2'-O-alkylation of 3',5'-di-O-tetraisopropyldisiloxane-1,3-diyl protected ribonucleosides with methyl iodide in the presence of silver (I) oxide. Because the 3'-hydroxyl group is protected from reaction, 2'-O-alkylation is highly selective. The primary disadvantage of this method is its complexity as illustrated by the large number of steps required to obtain 2'-O-alkylated ribonucleosides suitable for direct conversion to RNA synthons. Using this method to produce RNA synthons, one must protect the ribonucleoside with the tetraisopropyldisiloxane group, 2'-O-alkylate the ribonucleoside, remove the tetraisopropyldisiloxane protecting group, re-protect the 5'-hydroxyl group with the dimethoxytriphenylmethyl (DMT) protecting group and finally derivatize the 3'-hydroxyl group.

Sproat and coworkers have reported an improved alkylation procedure on purine ribonucleosides partially protected as 3'-5'-di-O-tetraisopropyldisiloxane-ribonucleotides. See Sproat et al., Nucl. Acids Res., (1990) 18: 41–49, Sproat et al., Nucl. Acids Res. (1991) 19: 733–738, Sproat et al., Nucleosides and Nucleotides, (1991) 10: 25–36 and Sproat et al., European Patent Application No. P 39.06.864.7. Generally, the 2'-hydroxyl group is alkylated with methyl iodide in the presence of at least one equivalent of a sterically hindered strong base. This base mediated process was similarly applied to allylations of the 2'-hydroxyl group. See Sproat, et al., Nucl. Acids Res., 1991. Although 2'-O-alkylation is highly selective, the method used to obtain 2'-O-alkylated RNA synthons is still complex because the tetraisopropyldisiloxane group is used.

Another disclosure reports enhanced selective alkylation of the 2'-hydroxyl group on unprotected cytidine ribonucleoside. See Wagner et al., Nucl. Acids Res., (1991) 19: 5965–5971. Generally, the disclosure teaches one to alkylate unprotected cytosine ribonucleosides with alkyl halide in the presence of sodium hydride. The 2' and 3'-O-methyl cytosine ribonucleoside products were obtained in a ratio of greater than 4/1, respectively. However, the authors found it necessary subsequently to protect the nucleobase C4-exocyclic amino group and 5'-hydroxyl group before the product could be purified effectively.

Traditionally, 2'-O-alkyl uridine ribonucleosides have been prepared by alkylating the 2'-hydroxyl group of uridine ribonucleosides. See Furukawa et al., Chem. Pharm. Bull. (1965) 13: 1273–1278., Robins et al., J. Org. Chem. (1974) 39: 1891–1899., Kamimura et al., Chem. Lett., (1982) 965–969; Welch et al., Chemica. Scand. (1983) 37: 147–150; and Pathak et al., Chemica. Scriptor (1986) 26: 135–139. Generally, these disclosures teach the direct alkylation of unprotected uridine ribonucleosides. The methods fail to produce product in high yield because the alkylation reaction is not selective for the 2'-hydroxyl group. Consequently, a relatively small amount of desired 2'-O-alkylated uridine ribonucleoside must be isolated laboriously from a rather crude mixture of products.

More recently, Wagner and coworkers alkylated a $N^3$-(2-cyanoethyl) protected 5'-O-dimethoxytriphenylmethyl-uridine ribonucleoside. See Wagner et al., (1991) Nucl. Acids Res. 19: 5965–5971. Protection of the $N^3$ nitrogen of the pyrimidine nucleobase and the 5'-hydroxyl group render these functional groups inert to alkylation. However, the procedure is non-selective for alkylation of the 2'-hydroxyl group over the 3'-hydroxyl group. Consequently, the desired 2'-O-alkylated uridine ribonucleosides must be laboriously isolated from the crude mixture of products thereby resulting in a poor yield (33% 2'-O-methyl partially protected uridine ribonucleoside and 20% 2'-O-ethyl partially protected uridine ribonucleoside).

Direct glycosylation of 2'-O-methylated ribose with uracil is an alternative approach. See Haines, A. H., Tetrahedron, (1973) 29: 2807 and Chanteloup et al., (1994) Tett. Lett., 35: 877–880. These procedures first require several steps to prepare the 2'-O-alkylated ribose sugar, followed by a glycosylation reaction which produces mixtures of $N^3$ and $N^1$ glycosylated ribonucleosides.

As discussed above, selective alkylation and allylation of the 2' hydroxyl group of uridine ribonucleosides has been reported by several investigators who utilize the 3',5'-O-tetraisopropyldisiloxane-1,3-diyl protecting group. See Nyilas et al., Acta. Chemica Scand., (1986) B40: 826–830., Inoue et al., Nucl. Acids Res. (1987) 15: 6131–6148, Sproat et al., Nucl. Acids Res., (1990) 18: 41–49, Sproat et al., Nucl. Acids Res. (1991) 19: 733–738, Sproat et al., Nucleosides and Nucleotides, (1991) 10: 25–36 and Sproat et al., European Patent Application No. P 39.06.864.7. This is currently the preferred method, albeit complex, for synthesizing uridine ribonucleosides on a preparative scale.

Studies of the decomposition of DNA oligomers under alkaline conditions have demonstrated that cytosine nucleobases, within the oligomer, deaminate to form uridine nucleobases. See Marian et al., J. Biol. Chem., (1950) 189: 533, Ulman et al., Biochimica et Biophysica Acta., (1973) 294: 396–404 and Wang et al., Biochimica et Biophysica Acta., (1982) 697: 371–377. The alkaline mediated deamination of cytosine nucleosides likewise has been studied. See Ulman et al.; Kochetkov et al., in "Organic Chemistry of Nucleic Acids", Part B., (1972) pp 381–397, Plenum Press, New York and Japanese Patent Applications No. JP 3024397, JP 48062772 and JP 51023511. Generally, these disclosures teach the alkaline mediated deamination of unprotected nucleosides in aqueous solutions at elevated temperatures. Bisulfite also has been shown to deaminate cytosine. See Shapiro et al., JACS., (1974) 96: 906–912. Conversion of cytosine to uridine has been described in both nucleosides and oligonucleotides. The bisulfite deamination reactions are acidic, and because the 5'-hydroxyl protecting group of an RNA synthon typically is acid labile, this deamination method is fundamentally unsuitable for one step synthesis of partially protected uridine ribonucleosides suitable for direct con[n]version to an RNA synthon. Finally, Martin and co-workers have described the preparative synthesis of 2'-O-methyl uridine ribonucleoside by nitrous acid mediated deamination of 2'-O-methyl cytosine ribonucleoside. See Martin et al., Biochem., (1968) 7: 1406–1412. These harsh acidic conditions are likewise unsuitable for one step preparation intermediates useful for preparing RNA synthons.

In light of the foregoing there is a need for a simple, generally applicable, method for the large scale 2'-O-derivatization of partially protected cytosine ribonucleosides. There is additionally a need for a method for the large scale deamination of partially protected 2'-O-derivatized cytosine ribonucleosides suitable to prepare the corresponding partially protected 2'-O-derivatized uridine ribonucleosides. There is further a need for a method to convert the partially protected 2'-O-derivatized pyrimidine ribonucleosides to RNA synthons suitable for the assembly of oligoribonucleosides containing 2'-O-derivatized pyrimidine nucleotide subunits.

SUMMARY OF THE INVENTION

Accordingly, the present invention is directed to a method for derivatizing a 2'-hydroxyl group of a partially protected cytosine ribonucleoside having an unprotected 2' and 3'-hydroxyl group, and method for deaminating a partially protected 2'-O-derivatized cytosine ribonucleoside. The present invention substantially obviates one or more of the problems due to the limitations and the disadvantages of the related art. The principle advantage of the present invention is the provision of a method for synthetic techniques for large scale production of 2'-O-derivatized uridine and cytosine RNA synthons which can be subsequently used in the preparation of synthetic oligoribonucleotides containing 2'-O-derivatized cytosine and/or uridine ribonucleotide subunits.

To achieve these and other advantages and in accordance with the purpose of the invention, as embodied and broadly described, the invention relates to a method for derivatizing the 2'-hydroxyl group of a partially protected cytosine ribonucleoside having an unprotected 2' and 3'-hydroxyl group wherein a partially protected cytosine ribonucleoside with at least one equivalent of metal salt catalyst, at least one equivalent of a hydrocarbon halide, and less than one equivalent of base under conditions sufficient to preferentially derivatize the 2'-hydroxyl group over the 3'-hydroxyl group in a ratio of better than 65:35, respectively.

In another aspect the invention includes a method for deaminating a partially protected 2'-O-derivatized cytosine ribonucleoside wherein a partially protected 2'-O-derivatized cytosine ribonucleoside with at least one equivalent of a hydroxide source under conditions sufficient to convert greater than 70% of said partially protected -O-derivatized cytosine ribonucleoside to the corresponding partially protected 2'-O-derivatized uridine ribonucleoside.

In yet another aspect the invention includes a method for producing a partially protected 2'-O-derivatized cytosine ribonucleoside useful in the production of a 2'-O-derivatized RNA synthons wherein a 5'-hydroxyl group protected, C-4 exocyclic amine group protected, cytosine ribonucleoside and reacting said cytosine ribonucleoside with a hydrocarbon halide in the presence of a metal salt catalyst and less than one equivalent of base, thereby preferentially producing a partially protected 2'-O-derivatized cytosine ribonucleoside.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification, illustrate several embodiments of the invention, and together with the description serve to explain the principles of the invention.

DETAILED DESCRIPTION

Figure 1:
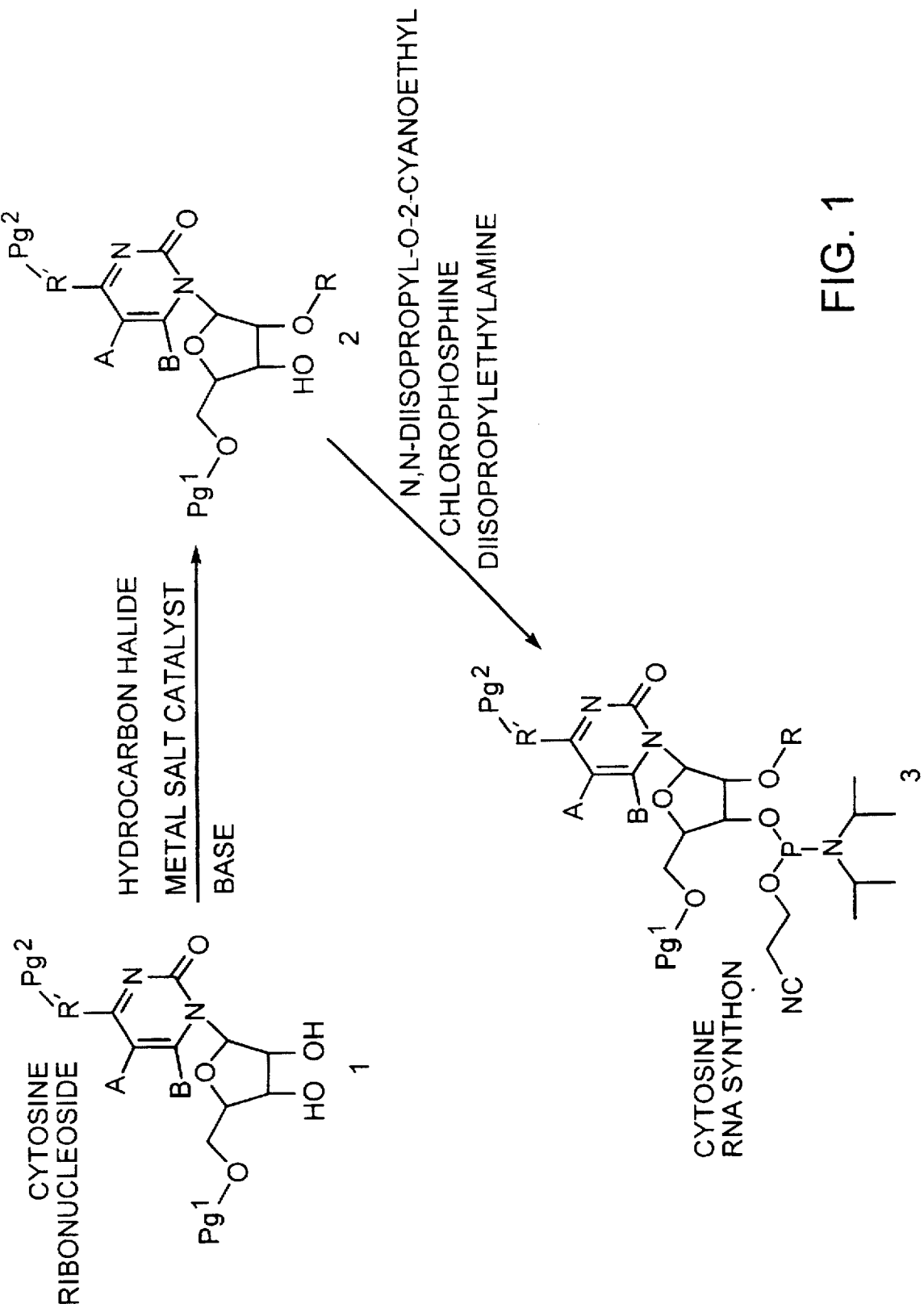
FIG. 1 is schematic representation of the selective derivatization of the 2'-hydroxyl group of a partially protected cytosine ribonucleoside. Formula 1, a partially protected cytosine ribonucleoside having an unprotected 2' and 3'-hydroxyl group is reacted with at least equivalent of hydrocarbon halide, at least one equivalent of metal salt catalyst and less than one equivalent of base to yield Formula 2, a partially protected 2'-O-derivatized cytosine ribonucleoside. The compound of Formula 2 is then directly converted to an RNA synthon, Formula 3, by procedures known in the art.

It has now been discovered that treatment of a partially protected cytosine ribonucleoside, bearing unprotected 2' and 3'-hydroxyl groups, with a hydrocarbon halide in the presence of a metal salt catalyst, preferably $Ag_2O$, and a base, present in amounts less than one equivalent of the amount of ribonucleoside, results in preferential 2'-O-derivatization of the ribonucleoside. This discovery provides a basis of design for novel synthetic techniques for large scale production of 2'-O-derivatized uridine and cytosine RNA synthons which can be subsequently used in the preparation of synthetic oligoribonucleotides containing 2'-O-derivatized cytosine and/or uridine ribonucleotide subunits.

As used herein, a partially protected cytosine ribonucleoside is a cytosine ribonucleoside containing one or more protecting groups wherein the 2' and 3'-hydroxyl groups remain unprotected. Typically, the C4 exocyclic amino group and/or the 5'-hydroxyl group will be protected. These protecting groups render the functional groups inert to reaction with the hydrocarbon halide. A metal salt catalyst is a metal salt which when present during the reaction of a hydrocarbon halide with the 2'-hydroxyl group of a cytosine ribonucleoside in the presence of base, increases reaction rate. Typical examples of such metal salts catalysts are silver oxide, tin oxide, tin chloride, silver chloride and silver triflate. A hydrocarbon halide is a hydrocarbon molecule having one reactive halide atom which can be reacted with the 2'-hydroxyl group of a cytosine ribonucleoside in the presence of a less than one equivalent of base and at least one equivalent of metal salt catalyst.

The desired 2'-O-derivatized product is prepared by the reaction of the 2'-hydroxyl group of the partially protected cytosine ribonucleoside with the hydrocarbon halide. Provided it does not render the halide unreactive, the hydrocarbon moiety of the hydrocarbon halide is not important to the derivatization reaction. Typically, the hydrocarbon portion will be a straight chain or branched alkyl or alkenyl group. Other preferred groups include dimethyl allyl, cinnamyl and 4-nitrocinnamyl.

In one aspect, the invention provides a method for a convenient, high yield, one step synthesis of partially protected 2'-O-derivatized cytosine ribonucleosides starting from partially protected cytosine ribonucleosides. Using the preferred embodiments, it is possible to achieve a high degree of preferential reaction of the 2'-hydroxyl group of partially protected cytosine ribonucleosides with a hydrocarbon halide in the presence of metal salt, preferably silver (I) oxide, and a base. For unknown reasons, the presence of less than one equivalent of base, most preferably less than one-half equivalent, dramatically enhances the selectivity of the derivatization reaction thereby permitting synthesis of predominately the partially protected 2'-O-derivatized cytosine ribonucleoside without generating significant amounts of 3'-O-alkylated or 2',3'-di-O-alkylated product.

More specifically this invention is directed to the 2'-O-derivatization of partially protected cytosine ribonucleosides of the formula:

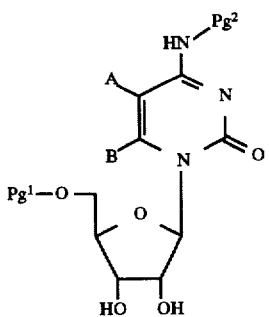

wherein $Pg^1$ is a protecting group suitable for protecting the 5'-hydroxyl group from derivatization and likewise increasing the solubility of the ribonucleoside in organic solvents. Typically, the protecting group is a sterically hindered lipophillic protecting group which is acid labile. Preferred protecting groups include, triphenylmethyl, 4-methoxytriphenylmethyl, 4,4'-dimethoxytriphenylmethyl, 4,4',4"-trimethoxytriphenylmethyl, 9-phenylxanthene-9-yl (pixyl), t-butyldimethylsilyl, triisopropylsilyl, triethylsilyl, ethyldiisopropylsilyl and ethyldiphenylsilyl. Preferably, $Pg^2$ is a protecting group suitable for protecting the C4 exocyclic amino group from alkylation and likewise increasing the solubility of the ribonucleoside in organic solvents. Typically, the protecting group is ammonia labile. Preferred protecting groups include, acetyl, isobutyryl, trimethylacetyl, benzoyl, phenoxyacetyl, t-butylphenoxyacetyl, dimethylformamide and diethylformamide. The atoms or groups represented by A and B is individually either hydrogen, methyl, ethyl, propyl, isopropyl, butyl, t-butyl, fluorine, chlorine, bromine and iodine.

Depending on reaction conditions and the selection of reagents, it is possible, using the process of the invention, to routinely obtain favorable ratios of 2'-O-derivatized over 3'-O-derivatized and 2,3-di-O-derivatized side products in excess of 5:1. Exploiting preferred conditions permits one to achieve favorable ratios of greater than 10:1. Under highly optimized conditions it is even possible to obtain mixtures of greater than 95:1. See entry #3 of table 1.

For unknown reasons, the present invention appears to be uniquely applicable to cytosine ribonucleosides. Curiously, it has been observed that similar selectivity of derivatization does not occur in the corresponding partially protected uridine, adenine or guanine ribonucleosides.

Nonetheless, it has further been discovered that a partially protected 2'-O-derivatized cytidine ribonucleoside, prepared as described above, can be reacted with at least one equivalent of a hydroxide source at elevated temperature, preferably between 50°–150° C., in aqueous solvent containing a water miscible organic solvent, wherein the organic solvent content can be varied and is preferably between 1 to 70%. The reaction proceeds to deaminate the C4 amino group of the partially protected 2'-O-derivatized cytidine ribonucleoside with minimal loss of the 5'-O-hydroxyl protecting group thereby generating predominantly the corresponding partially protected 2'-O-derivatized uridine ribonucleoside and only small amounts of by-product. Depending on reaction conditions and the selection of reagents, it is possible, using the process of the invention, to routinely obtain favorable deamination of the cytosine nucleobase without significant side product formation. Exploiting favorable conditions permits one to achieve conversion to greater than 70 percent of the desired partially protected 2'-O-derivatized uridine ribonucleoside.

Thus, in another aspect this invention, there is provided a method for a convenient, high yield, one step, synthesis of partially protected 2'-O-derivatized uridine ribonucleosides. As used herein a partially protected 2'-O-derivatized uridine ribonucleoside is a uridine ribonucleoside containing only a 5'-hydroxyl protecting group and a derivatized 2'-hydroxyl group. It has been observed that lithium hydroxide is particularly well suited for the specific deamination of cytosine ribonucleosides without producing a substantial loss of the 5'-hydroxyl protecting group or inducing rearrangement to 3'-O-derivatized partially protected ribonucleosides products.

More specifically, this invention is directed to the deamination of partially protected 2'-O-derivatized cytidine ribonucleosides of the formula:

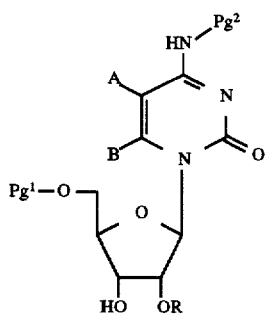

wherein the protecting group represented by $Pg^1$ is triphenylmethyl, 4-methoxytriphenylmethyl, 4,4'-dimethoxytriphenylmethyl, 4,4',4"-trimethoxytriphenylmethyl or 9-phenylxanthene-9-yl (pixyl). The protecting group represented by $Pg^2$ is acetyl, isobutyryl, trimethylacetyl, benzoyl, phenoxyacetyl, t-butylphenoxyacetyl, dimethylformamide or diethylformamide. The atom or group represented by A and B individually, hydrogen, methyl, ethyl, propyl, isopropyl, butyl or t-butyl. The hydrocarbon group represented by R is dimethylallyl, cinnamyl, 4-nitrocinnamyl, an alkyl group of the formula $C_nH_{2n+1}$ wherein n is an integer from 1–20 or an alkenyl group of the formula $C_nH_{2n-1}$ wherein n is an integer from 1–20. Preferably $Pg^1$ is 4,4'-dimethyoxytriphenylmethyl and R is methyl.

Now that it is possible to conveniently prepare partially protected 2'-O-derivatized cytosine and uridine ribonucleosides, in yet another aspect of this invention, from appropriately protected ribonucleosides, it is possible to prepare in one step by using conventional methods, the corresponding 2'-O-derivatized uridine and cytosine RNA synthons and then assemble oligoribonucleosides containing 2'-O-derivatized pyrimidine ribonucleotide subunits.

A general, convenient, high yield, one step method for synthesizing partially protected 2'-O-derivatized cytosine ribonucleosides having an unprotected 3'-hydroxyl group has been developed. By the method of this invention, a high degree of selective derivatization of the 2'-hydroxyl group of a partially protected cytosine ribonucleoside occurs in the presence of an unprotected 3'-hydroxyl group. Because the derivatization reaction proceeds in such a highly selective manner, the applicants demonstrate, for the first time, the one-step preparation of partially protected 2'-O-derivatized cytosine ribonucleosides suitable for direct conversion to cytosine RNA synthons.

With reference to FIG. 1, this invention is a method for selectively derivatizing the 2'-hydroxyl group of a partially protected cytosine ribonucleoside (1) having an unprotected 2' and 3'-hydroxyl group. According to the method, said partially protected cytosine ribonucleoside (1) is reacted with at least one equivalent of hydrocarbon halide, at least one equivalent of metal salt catalyst, preferably silver (I) oxide ($Ag_2O$), and less than one equivalent of base. The reaction proceeds at temperatures of about 20° C. to 30° C. in an aprotic organic solvent. Preferably the temperature is maintained between about 0° C. to 5° C. and the solvent is toluene. When using volatile hydrocarbon halides such as methyl iodide it is preferable to seal the reaction flask. The reaction proceeds to selectively derivatize the 2'-hydroxyl group of the partially protected cytosine ribonucleoside thereby generating predominantly the partially protected 2'-O-derivatized cytosine ribonucleoside (2). Typically the reaction is monitored and stopped when analysis determines that at least 90% of the starting material is consumed. Because the reaction is highly selective and the reaction products are lipophillic, the 2'-O-derivatized product can be easily purified by silica gel chromatography. Where the partially protected 2'-O-derivatized cytosine ribonucleoside is suitably protected for RNA synthesis, the purified product may be directly converted to an RNA synthon (3) by known procedures. See Sinha, N. et al., Nucl. Acids Res., (1984) 12: 4539–4557.

The partially protected cytosine ribonucleoside starting materials which are 2'-O-derivatized by the method of this invention are cytosine ribonucleosides having one or more protecting groups. The protecting groups increase the solubility of the cytosine ribonucleoside starting material in organic solvents and render the protected functional group inert to derivatization. Functional groups which are typically protected are the C4 exocyclic amino group and/or the 5'-hydroxyl group. The 5'-hydroxyl group protecting group is typically a sterically hindered lipophillic protecting group which is acid labile. The C4 exocyclic amino group protecting group is typically ammonia labile. Other moieties or functional groups may also be protected or modified provided that the cytosine ribonucleoside remain unprotected at the 2' and 3'-hydroxyl group. The examples in Tables 1–3 demonstrate that selective 2'-O-derivatization occurs despite changes in the protecting groups.

In a preferred embodiment, said partially protected cytosine ribonucleoside starting material has the formula:

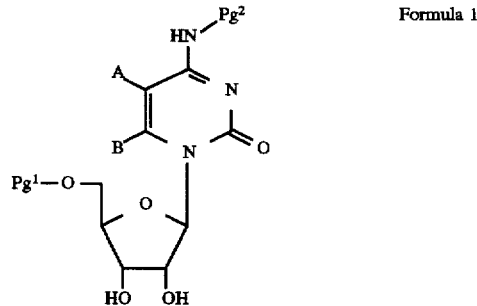

Formula 1 wherein the protecting group represented by $Pg^1$ is triphenylmethyl, 4-methoxytriphenylmethyl, 4,4'-dimethoxytriphenylmethyl, 4,4',4"-trimethoxytriphenylmethyl, 9-phenylxanthene-9-yl (pixyl), t-butyldimethylsilyl, triisopropylsilyl, triethylsilyl, ethyldiisopropylsilyl or ethyldiphenylsilyl. The protecting group represented by $Pg^2$ is acetyl, isobutyryl, trimethylacetyl, benzoyl, phenoxyacetyl, t-butylphenoxyacetyl, dimethylformamide or diethylformamide. The atom or group represented by A and B is individually, hydrogen, methyl, ethyl, propyl, isopropyl, butyl, t-butyl, fluorine, chlorine, bromine or iodine.

When alkylated by the method of this invention, starting materials of preferred composition yield 2'-O-derivatized products which are suitable for direct conversion to RNA synthons using conventional methods which involve reaction of the 3'-hydroxyl group with a phosphitylation reagent. See Gait et al., Oligonucleotides and Analogs: A Practical Approach., Fritz Eckstein, Editor, (1991) Oxford University Press, Oxford. pp 25–48. This result is possible because the 5'-hydroxyl group and the C4 exocyclic amino group of the cytosine ribonucleoside is appropriately protected and these protecting groups ($Pg_1$, $Pg_2$) are stable to the derivatization conditions. One preferred partially protected cytosine ribonucleoside starting material of this invention is:

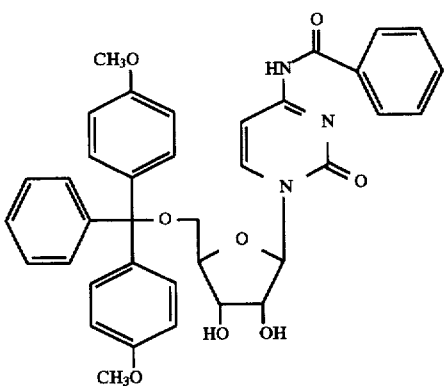

Formula 6

The applicants successfully prepared the corresponding RNA synthon in two steps comprised of: 1) 2'-derivatization according to the method of this invention and 2) phosphitylation according to known procedures. See Sinha, N. et al., Nucl. Acids Res., (1984) 12: 4539–4557. Another preferred partially protected cytosine ribonucleoside starting material of this invention is:

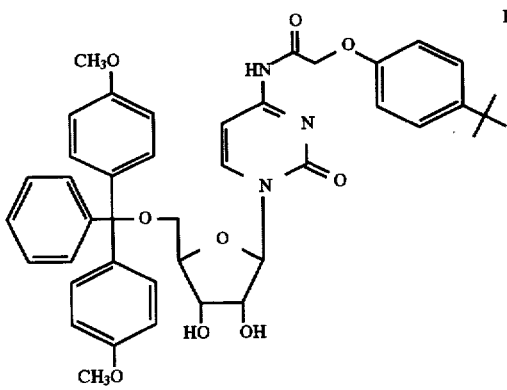

Formula 7

Likewise, a novel corresponding 2'-O-derivatized RNA synthon was prepared in 2 steps comprised of: 1) 2'-O-derivatization according to the method of this invention (See Example 1); followed by 2) phosphitylation according to known procedures. (See Example 2) (Id.)

A metal salt catalyst is a metal salt which, when present during the reaction of the hydrocarbon halide with the partially protected cytosine ribonucleoside in the presence of base, increases reaction rate. Silver (I) oxide is well known for catalyzing such derivatization reactions in nucleosides. Other examples of such metal salt catalysts include, but are not limited to tin oxide, tin chloride, silver chloride and silver triflate.

Hydrocarbon halides are known to be strong alkylating reagents (See Solomons, T. W. G., Organic Chemistry, (1984) J. Wiley and Sons, New York, 177–200). Typically, the iodides are preferred because they are more reactive than the bromides and chlorides. By the method of this invention a hydrocarbon halide is reacted with the 2'-hydroxyl group of a partially protected cytosine ribonucleoside thereby derivatizing the 2'-hydroxyl group. At least one equivalent of hydrocarbon halide is required but typically a substantial excess of hydrocarbon halide is used. Preferably, about 2–30 equivalents of hydrocarbon halide is added to the reaction.

The reaction is simple in scope and the various examples shown in Table 1 demonstrate the versatility of this method for producing cytosine ribonucleosides bearing several 2'-O substituents. It should be further noted that numerous hydrocarbon halides are readily available. See Classes of Compounds and Numerical Cross Reference List: Supplement to the Aldrich Catalog Handbook of Fine Chemicals 1990 (Aldrich Chemical Company, Milwaukee, Wis.). The hydrocarbon portion of the hydrocarbon halide must be inert during the derivatization reaction but otherwise very few limitations of structure exist. Consequently in one embodiment, the hydrocarbon halide is a straight chain or branched alkyl halide of the formula $C_nH_{2n+1}X$ wherein n is an integer from 1 to 20 and X is a halogen atom. In a preferred embodiment the alkyl halide is methyl iodide, ethyl iodide, propyl iodide or pentyl iodide.

TABLE 1

| Entry # | Alkyl Iodide* | Equiv. Silver (I) Oxide | Temp. Range °C. | Rxn Time Hrs | % Products** (A, B, C) |
|---|---|---|---|---|---|
| 1 | methyl | 2.5 | 0–5 | 3 | 91, 5, 3 |
| 2 | allyl | 2.5 | 0–5 | 4 | 74, 2, 9 |
| 3 | ethyl | 2.5 | 0–10 | 10 | 98, 0, 1 |
| 4 | propyl | 2.5 | 0–25 | 22 | 76, 2, 3 |
| 5 | pentyl | 2.5 | 0–25 | 48 | 30, 1, 51 |

All starting material had $Pg^1$ as the 4,4'-dimethoxytriphenylmethyl (DMT) protecting group. All starting material had $Pg^2$ as the t-butylphenoxyacetyl protecting group. The reaction scale of all reactions was 1 gram and the base was pyridine (0.2 equivalents).
*Equivalents for all alkyl iodide were 25.
A = 2'-O-methyl cytosine ribonucleoside.
B = 2'3-O,O-dialkyl cytosine ribonucleoside,
C = starting material.
**Anaylsis was performed by HPLC on the crude product.
Analysis conditions: Mobile phase 40–85% gradient;
Buffer A = Hexane;
Buffer B = EtOAc w/1% MeOH;
Stationary phase = Silica (Nova Pak-Silica, 3.9 × 150 mm).

In another embodiment, the hydrocarbon halide is an alkenyl halide of the formula $C_nH_{2n-1}X$ wherein n is an integer from 1 to 20 and X is a halogen atom. A preferred alkenyl halide is allyl iodide. Alternately, the hydrocarbon moiety may be unsaturated but of differing composition. Other preferred unsaturated hydrocarbon halides include, but are not limited to dimethylallyl halide, cinnamyl halide and 4-nitrocinnamyl halide.

Silver (I) oxide mediated derivatizations are known to be very selective for the 2'-hydroxyl group where the 3'-hydroxyl group is protected. See Sproat et al., Nucl. Acids Res., (1990) 18: 41–49. Sproat et al., Nucl. Acids Res. (1991) 19: 733–738. Sproat et al., Nucleosides and Nucleotides, (1991) 10: 25–36 and Sproat et al., European Patent Application No. P 39.06.864.7 and Srivastava et al., U.S. Pat. No. 5,214,135. The applicants are unaware of any report describing the silver (I) oxide mediated alkylation of a ribonucleoside with a hydrocarbon halide in the presence of a base. It has now been surprisingly discovered that the presence of less than one equivalent of base enhances the selectively of the derivatization reaction thereby allowing for the selective 2'-O-derivatization of partially protected cytosine ribonucleosides wherein both the 2' and 3'-hydroxyl groups remain unprotected.

Table 2 demonstrates that without any base, 2' and 3'-O-alkylation proceed in relatively equal amounts. See Entries 1-3, 9, 13-16. Where 0.1 to 0.25 equivalents of base is used the selectivity is dramatically enhanced. With reference to entry number 19, the applicants have determined that less selectivity is exhibited where 0.4 equivalents of base is added. In fact, it has been determined that the beneficial effect of base substantially decreases where greater than 0.5 equivalent is added. Thus, preferably about 0.1 to 0.5 equivalents of base is added; more preferably about 0.1 to 0.25 equivalents of base is added.

Table 3 demonstrates that numerous bases exhibit the observed enhancement of selectivity of the alkylation reaction. The base may be inorganic or organic but is preferably organic. Several bases shown to be effective are N,N-dimethylamino pyridine;, N,N-diisopropylethylamine;, quinolone and 2-tert Butylimino-2-diethylamino-1,3-dimethylperhydro-1,3,2-diasaphosphorine. Preferably, the base is a substituted pyridine. Suitable substituted pyridines are sym-collidine and 2,6-lutidine. In the most preferred embodiment the base is pyridine.

By careful analysis of the data in Tables 2 and 3 it becomes obvious that the method of this invention is very versatile. The method can be easily scaled between 1 to 132 grams. See Table 2, entries 6, 12, 17 and 20. This is especially useful given the current need to scale up reactions to fulfill current commercial demand. Further, the reaction proceeds at various equivalents of hydrocarbon halide and protecting groups can be interchanged without destroying the selectivity of the alkylation reaction.

TABLE 2

| Entry # | Pg² | Rxn Scale (g) | Methyl Iodide (equiv.) | Base | Equv. Base | Equiv. Silver (I) Oxide | Temp Range °C. | Rxn Time | % Products** (A, B, C, D) |
|---|---|---|---|---|---|---|---|---|---|
| 1 | Bz | 5 | 25 | none | 0 | 2.5 | 25 | 3 h | 38, 27, 2, 28 |
| 2 | Bz | 50 | 1.5 | none | 0 | 2.5 | 25 | 7 d | 63, 26, 6, 3 |
| 3 | Bz | 50 | 25 | none | 0 | 2.5 | 25 | 24 h | 46, 35, 4, 7 |
| 4 | Bz | 1 | 25 | pyridine | 0.2 | 1.5 | 0–23 | 5 h | 50, 16, 24, 5 |
| 5 | t-BPA | 1 | 2 | pyridine | 0.1 | 2.5 | 25 | 7 d | 81, 13, 6 |
| 6 | t-BPA | 1 | 25 | pyridine | 0.1 | 2.5 | 0–5 | 7 h | 93, 1, 3 |
| 7 | t-BPA | 1 | 25 | pyridine | 0.2 | 2.5 | 0–5 | 3 h | 91, 5, 3 |
| 8 | t-BPA | 3 | 3 | pyridine | 0.2 | 2.5 | 25 | 11 d | 80, 9, 3, 2 |
| 9 | t-BPA | 5 | 6 | none | 0 | 2.5 | 25 | 10 d | 42, 47, 6, 3 |
| 10 | t-BPA | 5 | 2.5 | pyridine | 0.2 | 2.5 | 25 | 10 d | 83, 6, 7 |
| 11 | t-BPA | 5 | 25 | pyridine | 0.2 | 2.5 | 0–5 | 3 h | 91, 3, 4 |
| 12 | t-BPA | 15 | 25 | pyridine | 0.1 | 2.5 | 0–5 | 7 h | 89, 1, 5 |
| 13 | t-BPA | 30 | 25 | none | 0 | 2.5 | 0–5 | 36 h | 57, 19, 7 |
| 14 | t-BPA | 35 | 3.5 | none | 0 | 2.5 | 25–45 | 14 d | 46, 36, 14 |
| 15 | t-BPA | 38 | 6 | none | 0 | 2.5 | 25 | 22 d | 63, 34, 4, 2 |
| 16 | t-BPA | 50 | 25 | none | 0 | 2.5 | 0–5 | 2 d | 55, 14, 23 |
| 17 | t-BPA | 50 | 25 | pyridine | 0.1 | 1.5 | 0–5 | 9 h | 92, 1, 5 |
| 18 | t-BPA | 100 | 25 | pyridine | 0.2 | 2.5 | 0–5 | 7 h | 80, 5, 7 |
| 19 | t-BPA | 100 | 25 | pyridine | 0.4 | 2.5 | 0–5 | 1.5 h | 65, 23, 3 |
| 20 | t-BPA | 132 | 25 | pyridine | 0.1 | 2.5 | 0–5 | 17 h | 83, 5, 2 |

All starting material had Pg¹ as the 4,4'-dimethoxytriphenylmethyl (DMT) protecting group.
Bz = benzoyl,
t-BPA = t-butylphenoxyacetyl.
A = 2'-O-methyl cytosine ribonucleoside.
B = 2',3'-O,O-dialkyl cytosine ribonucleoside,
C = starting material.
D = other unidentified product.
**Analysis was performed by HPLC on the crude product.
Analysis conditions: Mobile phase 40–85% gradient;
Buffer A = Hexane;
Buffer B = EtOAc w/1% MeOH;
Stationary phase = Silica (Nova Pak-Silica, 3.9 × 150 mm).

TABLE 3

| Entry # | Pg² | Base | Equiv. Silver (I) Oxide | Temp. Range °C. | Rxn Time hrs | % Product** (A, B, C, D) |
|---|---|---|---|---|---|---|
| 1 | Bz | pyridine | 1.5 | 0–23 | 5 | 50, 16, 24, 5 |
| 2 | Bz | DBU | 1.5 | 0–23 | 4 | 32, 11, 40, 14 |
| 3 | Bz | DMAP | 1.5 | 0–23 | 4 | 29, 16, 21, 27 |
| 4 | t-BPA | pyridine | 2.5 | 0–5 | 3 | 91, 5, 3 |
| 5 | t-BPA | 2,6-lutidine | 1.5 | 0–5 | 35 | 83, 3, 6 |
| 6 | t-BPA | sym-collidine | 1.5 | 0–5 | 9 | 91, 2, 2 |
| 7 | t-BPA | DBU | 1.5 | 0–5 | 2.5 | 94, 1, 3 |
| 8 | t-BPA | BDDDP | 1.5 | 0–5 | 8 | 66, 16, 4 |
| 9 | t-BPA | quinoline | 1.5 | 0–5 | 15 | 84, 3, 2 |
| 10 | t-BPA | DiPEA | 1.5 | 0–5 | 18 | 77, 9, 3 |
| 11 | t-BPA | DMAP | 1.5 | 0–5 | 1 | 86, 7, 2 |
| 12 | t-BPA | DMAP | 0 | 0–5 | 17 | 6, 0, 87 |

All starting material had Pg¹ as the 4,4'-dimethoxytriphenylmethyl (DMT) protecting group. The reaction scale was 1 gram. The equivalents of methyl iodide and base were 25 and 0.2 respectively.
Bz = benzoyl,
TAC = t-butylphenoxyacetyl.
DBU = 1,8-Diazabicyclo[5.4.0]undec-7-ene,
DMAP = dimethylaminopyridine,
BDDDP = 2-tert-Butylimino-2-diethylamino-1,3-dimethylperhydro-1,3,2-diazaphosphorine,
DiPEA = Diisopropylethylamine.
A = 2'-O-methyl cytosine ribonucleoside.
B = 2',3'-O,O-dimethyl cytosine ribonucleoside,
C = starting material,
D = other unidentified product.
**Analysis was performed by HPLC on the crude product.
Analysis conditions: Mobile phase 40–85% gradient;
Buffer A = Hexane;
Buffer B = EtOAc w/1% MeOH;
Stationary phase = Silica (Nova Pak-Silica, 3.9 × 150 mm).

This invention is further directed to a convenient, high yield, one step method for the preparation of partially protected-2'-O-derivatized uridine ribonucleosides by the deamination of the corresponding partially protected 2'-O-derivatized cytidine ribonucleosides. Deamination occurs by reaction with a hydroxide source in aqueous solvents containing water miscible organic solvents. Because deamination occurs without substantially removing the 5'-hydroxyl protecting group, the applicants have determined that by judicious choice of starting materials it is possible to prepare, in one step, the partially protected 2'-O-derivatized uridine ribonucleosides suitable for direct conversion to uridine synthons for RNA synthesis.

Figure 2:
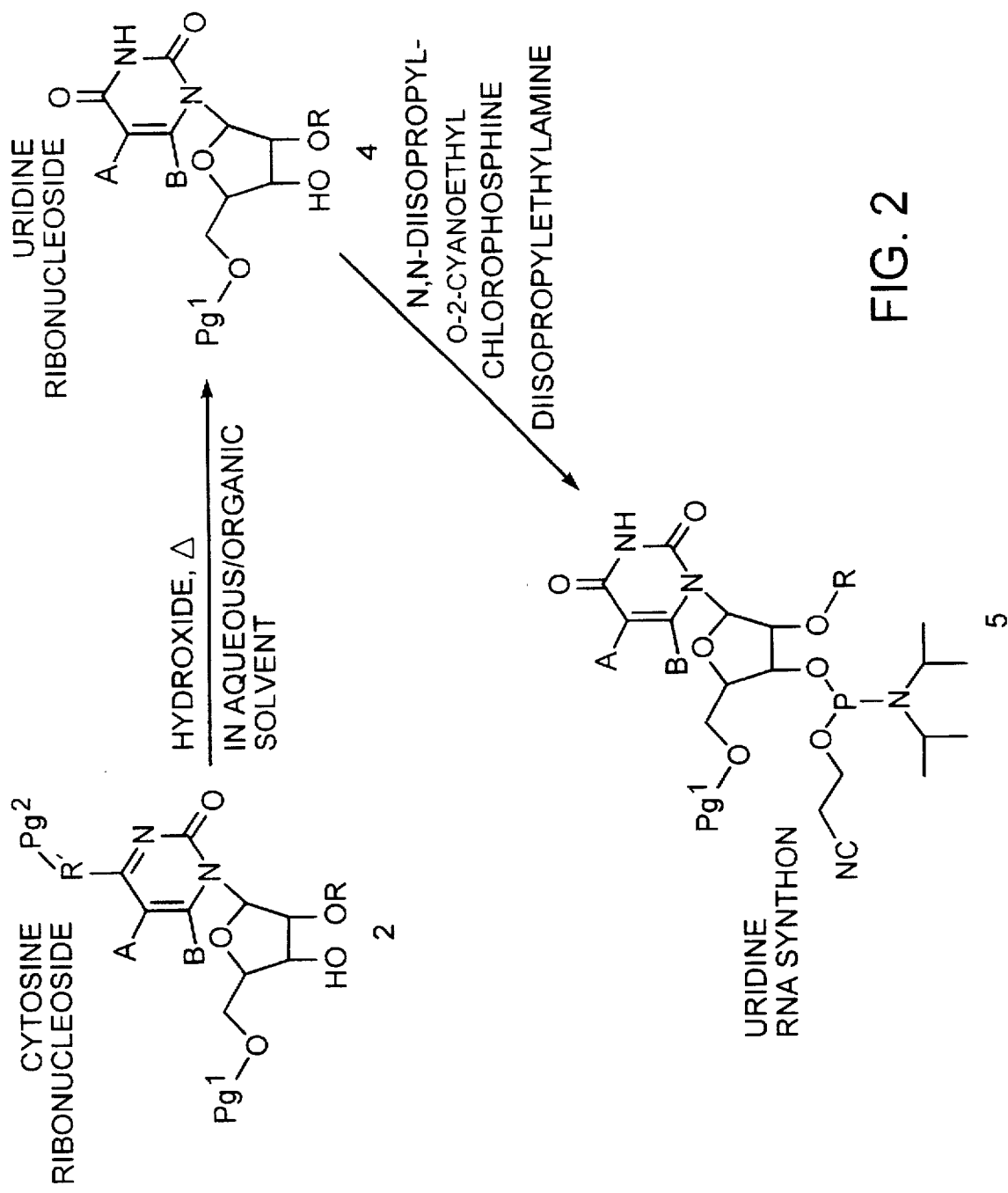
FIG. 2 is a schematic representation of the deamination on of a partially protected 2'-O-derivatized cytosine ribonucleoside, which is reacted with at least one equivalent of hydroxide in aqueous solvent containing a water miscible organic solvent. The resulting partially protected 2'-O-derivatized uridine ribonucleoside, Formula 4, can then be directly converted to Formula 5, a uridine RNA synthon.

With reference to FIG. 2, a partially protected 2'-O-derivatized cytidine ribonucleoside (Formula 2) is reacted with at least one equivalent of hydroxide at temperatures between about 50°–150° C. in aqueous solvent containing a water miscible organic solvent, wherein the organic solvent content varies between about 1 to 70%. The reaction proceeds to quantitatively deaminate the C4 amino group of the partially protected 2'-O-derivatized cytidine ribonucleoside analog with minimal loss of the 5'-O-hydroxyl protecting group thereby generating predominantly the partially protected 2'-O-derivatized uridine ribonucleoside (Formula 4) and only very small amounts of by-products. Thereafter, the crude product can be easily purified by column chromatography.

The partially protected 2'-O-derivatized cytosine ribonucleoside will have a 5'-hydroxyl protecting group (Pg¹) which is relatively stable to the alkaline deamination reaction. Typically, the protecting group is a sterically hindered lipophillic protecting group which is acid labile. Preferably, the protecting group is a triphenylmethyl (trityl) derivative. Most preferably, the protecting group is the 4,4'-dimethoxytriphenylmethyl (DMT) group which is the benchmark 5'-hydroxyl protecting group for DNA and RNA synthons. Stability of the protecting group insures that no further manipulation of the partially protected 2'-O-derivatized uridine ribonucleoside (4) need be performed prior to RNA synthon formation.

Typically said partially protected 2'-O-derivatized cytosine ribonucleosides starting material (2) will be protected (Pg²) at C4 exocyclic amino group of the pyrimidine base. Preferred protecting groups will be those commonly used for DNA and RNA synthons. Thus, Pg² is preferably selected from the group consisting of acetyl, isobutyryl, trimethylacetyl, benzoyl, phenoxyacetyl, t-butylphenoxyacetyl, dimethylformamide and diethylformamide. However, one may optionally use a partially protected cytosine ribonucleoside having no protection of the C4 exocyclic amino group since deamination occurs whether or not protected.

The reaction proceeds in aqueous solvents containing water miscible organic solvents. Organic solvent composition is chosen such that the partially protected 2'-O-derivatized cytosine ribonucleoside is soluble in the refluxing solution. Alcohols such as methanol and ethanol are particularly well suited to aiding in the solubility of the partially protected 2'-O-derivatized cytosine ribonucleoside. The reaction is heated and preferably allowed to reflux. Thus, the reaction temperature is often defined by the solvent composition. Preferred reaction temperatures are between about 50°–150° C.

The alkaline conditions used to deaminate the pyrimidine nucleobase are generated with a hydroxide source (See Table 4). Cesium hydroxide, potassium hydroxide, sodium hydroxide, lithium hydroxide and ammonium hydroxide are suitable hydroxide sources. The applicants have determined that lithium hydroxide is particularly well suited to performing the method of this invention.

The extensive entries in Table 4 demonstrate the overall versatility of this method. Entries 1 to 7 demonstrate that the method is applicable despite the composition of the 2'-O-derivatized group. Entries 16 to 19 demonstrate that the reaction is easily scaled up. This is critical to enable the large scale synthesis which is needed to provide product to the growing market. As demonstrated by further consideration of Table 4, large variations in hydroxide source, solvent composition and temperature are also permissible. Despite these numerous variations, product is always obtained and the yield is usually good.

TABLE 4

| Entry # | Alkyl Halide | Rxn Scale (g) | Hydroxide | Temp °C. |
|---|---|---|---|---|
| 1 | 1(methyl) | 1 | 4M NaOH | 110 |
| 2 | 1(methyl) | 72 | 4M NaOH | 110 |
| 3 | 2(allyl) | 1 | 4M NaOH | 110 |
| 4 | 2(allyl) | 0.6 | 4M NaOH | 110 |
| 5 | 3(ethyl) | 1 | 4M NaOH | 110 |
| 6 | 4(propyl) | 0.7 | 4M NaOH | 110 |
| 7 | 5(propyl) | 0.8 | 4M NaOH | 110 |
| 8 | 1(methyl) | 1 | 4M KOH | 110 |
| 9 | 1(methyl) | 1 | 2M LiOH | 90 |
| 10 | 1(methyl) | 1 | 2M LiOH | 80 |
| 11 | 1(methyl) | 5 | 2M LiOH | 110 |
| 12 | 1(methyl) | 10 | 2M LiOH | 105 |
| 13 | 1(methyl) | 1 | 4M LiOH | 80 |
| 14 | 1(methyl) | 1 | 4M LiOH | 95 |
| 15 | 1(methyl) | 1 | 4M LiOH | 100 |
| 16 | 1(methyl) | 1 | 4M LiOH | 100 |
| 17 | 1(methyl) | 20 | 4M LiOH | 100 |
| 18 | 1(methyl) | 30 | 4M LiOH | 100 |
| 19 | 1(methyl) | 80 | 4M LiOH | 100 |

| Entry # | Solvent | Rxn Time hrs or days | Yield % | Ratio (E:F*) |
|---|---|---|---|---|
| 1 | H₂O:dioxane (1:1) | 48 h | 60 | 7:1 |
| 2 | H₂O:dioxane (1:1) | 5 d | 52 | 10:1 |
| 3 | H₂O:dioxane (1:1) | 24 h | 27 | 20:1 |
| 4 | H₂O:dioxane (1:1) | 3 d | 59 | 10:1 |
| 5 | H₂O:dioxane (1:1) | 3 d | 53 | 7:1 |
| 6 | H₂O:dioxane (1:1) | 3 d | 59 | 24:1 |
| 7 | H₂O:dioxane (1:1) | 3 d | 55 | 100:1 |
| 8 | H₂O:dioxane (1:1) | 24 h | 30 | 7:1 |
| 9 | EtOH:H₂O:dioxane | 24 h | 60 | 7:1 |
| 10 | EtOH:H₂O:dioxane (1:1:1) | 48 h | 50 | 7:1 |
| 11 | H₂O:dioxane (1:1) | 24 h | 50 | 7:1 |
| 12 | H₂O:dioxane:MeOH (1:0.8:0.2) | 24 h | 60 | 7:1 |
| 13 | H₂O:MeOH (1:9) | 48 h | 56 | 7:1 |
| 14 | H₂O:MeOH (1:1) | 24 h | 64 | 13:1 |
| 15 | H₂O | 16 h | 51 | 11:1 |
| 16 | H₂O:MeOH (9:1) | 24 h | 60 | 10:1 |
| 17 | H₂O:MeOH (4:1) | 16 h | 80 | 13:1 |
| 18 | H₂O:MeOH (4:1) | 6 h | 74 | 16:1 |
| 19 | H₂O:MeOH (4:1) | 8 h | 60 | 16:1 |

All starting material had Pg¹ as the 4,4'-methoxytriphenylmethyl (DMT) protecting group.
E = 2'O-alkyl uridine ribonucleoside and
F = 3'-O-alkyl uridine ribonucleoside.
*Analysis was performed by HPLC on the crude product.
Analysis conditions: Mobile phase 10–20% gradient in 20 minutes;
Buffer A = hexane;
Buffer B = ethylacetate with 1% methanol; Flow rate 2 mL/min;
Stationary Phase = Waters μBoundpack CN (R.P.) 3.9 × 150 mm.

Given the opportunity to substantially alter parameters, the conditions should be chosen to minimize side product formation. The applicants have observed only 2 side reactions. First, the 5'-hydroxyl group (DMT) has not proven to be completely stable during the deamination reaction. Typically, 1–5% of the ribonucleoside is detritylated. Additionally, by an unknown mechanism, migration of the 2'-O-derivatized group occurs in roughly 1–13% of the ribonucleoside thereby generating 3'-O-derivatized ribonucleoside. Conditions can be optimized by the use of lithium hydroxide as the alkaline base and by manipulating the organic co-solvent concentration to help in dissolution of the normally water insoluble protected cytosine ribonucleoside starting material. These conditions minimize both the detritylation and the 2' to 3' O-derivatized migration side reactions especially prevalent in larger reaction scales. See entries No. 18 and 19, Table 4. Because side reactions are minimal despite substantial variations in the conditions, the method is very versatile.

More specifically, this invention is directed to the deamination of partially protected 2'-O-derivatized cytidine ribonucleosides of the formula:

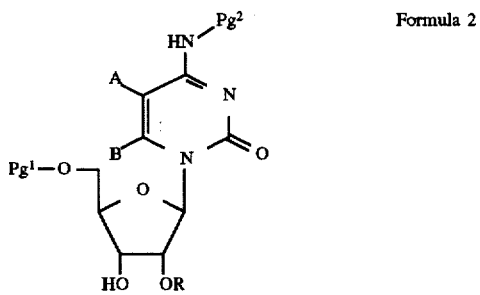

Formula 2 wherein the protecting group represented by Pg¹ is triphenylmethyl, 4-methoxytriphenylmethyl, 4,4'-dimethoxytriphenylmethyl, 4,4',4"-trimethoxytriphenylmethyl or 9-phenylxanthene-9-yl (pixyl). The protecting group represented by Pg² is acetyl, isobutyryl, trimethylacetyl, benzoyl, phenoxyacetyl, t-butylphenoxyacetyl, dimethylformamide or diethylformamide. The atom or group represented by A and B individually is, hydrogen, methyl, ethyl, propyl, isopropyl, butyl or t-butyl. The hydrocarbon group represented by R is dimethylallyl, cinnamyl, 4-nitrocinnamyl, an alkyl group of the formula $C_nH_{2n+1}$ wherein n is an integer from 1–20, an alkenyl group of the formula $C_nH_{2n-1}$ wherein n is an integer from 1–20, or a biotin, fluorescense, dioxetane label. Preferably Pg¹ is 4,4'-dimethyoxytriphenylmethyl and R is methyl.

Now that it is possible to conveniently prepare partially protected 2'-O-derivatized cytosine and uridine ribonucleosides, in yet another aspect of this invention, from appropriately protected ribonucleosides, it is possible to prepare in one step by using conventional methods, the corresponding 2'-O-derivatized uridine and cytosine RNA synthons and then assemble oligoribonucleosides containing 2'-O-derivatized pyrimidine ribonucleotide subunits.

The invention, being generally described above, is now more specifically illustrated by way of the following example(s), which are not meant to limit the invention, unless otherwise noted.

EXAMPLES

Example 1

Synthesis of 2'-O-methyl-5'-O-dimethoxytrityl-N⁴-t-butylphenoxyacetyl-cytidine

To a solution of 5'-O-dimethoxytrityl-N⁴-t-butylphenoxyacetyl-cytidine (100 g, 0.136 mole; Biosearch, USA) in 800 mL dry toluene was added silver (I) oxide (48 g, 0.21 mole; Aldrich P/N 22,116-3) and dry pyridine (1 mL, 0.014 mole; Baker P/N 9393-03). The reaction vessel was then capped and secured in an ice bath at 0°–5° C. and allowed to equilibrate for 15 minutes. When the solution had reached between 0°–5° C., methyl iodide (210 mL, 3.4 moles; Aldrich P/N I,850-7) was added. The vessel was tightly capped and allowed to stir at 0°–5° C. The reaction was analyzed by thin-layer chromatography every hour. When analysis indicated that less than 10% starting material remained (3 hrs), the flask was removed from the ice bath and the solution was quickly filtered through a plug of celite to remove excess silver (I) oxide. The filtrate was then evaporated to near dryness. The residue was redissolved in 800 mL of ethyl acetate and then extracted with 500 mL of a 5% solution of aqueous sodium iodide buffered with 1M sodium citrate pH (6.0). The pH of the aqueous layer was maintained below 8.0 to minimize the basicity of the solution upon formation of sodium hydroxide (a by-product of the sodium iodide/silver oxide quench). The aqueous layer was adjusted with more 1M sodium citrate pH 6.0 as required to maintain pH between 6.0–8.0. The heterogeneous solution was filtered through a celite plug if a large amount of precipitate (silver iodide) formed. The sodium iodide extraction procedure was repeated on the organic layer (keeping the pH between 6.0–8.0) until no more appreciable precipitate formed. The remaining organic layer was dried over sodium sulfate, filtered and evaporated to a foam. The product was then purified by silica gel chromatography (hexane: ethyl acetate: methanol, 30:69:1) to yield 87 g (85%) 5'-O-dimethoxytrityl-$N^4$-t-butylphenoxyacetyl-2'-O-methyl-cytidine.

$^1$H NMR (CDCl$_3$) δ9.23 (1H, br s), 8.62 (1H, d), 7.50–7.25 (11H, m), 7.12 (1H, d), 6.88 (6H, d), 6.01 (1H, s), 4.61 (2H, s), 4.46 (1H, m), 4.02 (1h, dt), 3.82 (6H, s), 3.79 (1H, d) 3.74 (3H, s), 3.59 (2H, ddd), 2.61 (1H, br d), 1.31 (9H, s).

Example 2

Synthesis of 2'-O-methyl-5'-O-dimethoxytrityl-$N^4$-t-butylphenoxyacetyl-cytidine-3'-O-(O-2-cyanoethyl N,N-diisopropyl) phosphoramidite To a 1 L flask containing 100 g dried (co-evaporated from dry toluene) 2'-O-methyl-5'-O-dimethoxytrityl-$N^4$-t-butylphenoxyacetyl-cytidine was added 500 mL of dry THF (Fluka, P/N 87371). The flask was sealed tightly with a rubber septum and purged with a stream of argon while stirring. To the briskly stirring solution was added 57 mL, (2.5 eq.) of freshly distilled diisopropylethylamine (Aldrich, P/N D12,580-6). Finally, 40 mL, (1.3 eq.) of O-β-cyanoethyl, N,N-diisopropyl chlorophosphine (Biosearch, P/N JGBY70000) was added using a dry, argon purged, 60 mL glass syringe with stainless steel needle. The reaction was analyzed for completion by TLC (mobile phase was neat ethyl acetate). When complete (2 hrs), the reaction was transferred to a rotavap and evaporated to 200 mL (approximate) under high vacuum with no heat. The solution was then cooled to 0° C. and the white salts filtered off. The white salts were washed with 100 mL ice cold, argon purged, ethyl acetate. The combined filtrates were then transferred to a 2 L separatory funnel and 400 mL ice cold, argon purged, ethyl acetate and 300 mL ice cold, argon purged, aqueous 5% sodium bicarbonate was also added. The product was extracted by thorough mixing and venting. The ethyl acetate layer was then separated, dried over 20 g sodium sulfate (30 minutes) in a sealed flask and then filtered. The sodium sulfate was washed once with cold ethyl acetate. The combined filtrates were then evaporated under high vacuum and low heat. The off white foam was dried overnight under high vacuum at room temperature. The final product was isolated by silica gel chromatography using a gradient of 30–100% ethyl acetate/hexane containing 0.5% pyridine. Yield 106 grams (84% yield) 2'-O-methyl-5'-O-dimethoxytrityl-$N^4$-t-butylphenoxyacetyl-cytidine-3'-O-(O-β-cyanoethyl, N,N-diisopropyl) phosphoramidite as a mixture of two diastereomers.

$^{31}$P NMR (CDCl$_3$) δ151.48 (1P, s), 150.96 (1P, s)

$^1$H NMR (CDCl$_3$) δ9.42 (2H, br s), 8.68 (1H, d), 8.48 (1H, d), 7.5–7.1 (28H, m), 7.05 (1H, d), 6.95 (1H, d), 6.9–6.8 (12H, m), 5.98 (1H, s), 5.93 (1H, s), 4.59 (4H, br s), 4.27 (2H, br d), 3.91 (2H, m), 3.81 (12H, s), 3.72 (2H, m), 3.67 (6H, s), 3.64–3.43 (8H, m), 2.59 (2H, t), 2.38 (2H, t), 2.33 (4H, s), 1.30 (18H, s), 1.21–1.09 (18H, m), 1.00 (6H, d).

Example 3

General Alkylation Procedure

Reagent equivalents can be deduced from data in Tables 1–3. If the table so indicates, the reagent was not added. To a solution of the partially protected cytosine ribonucleoside in dry toluene was added silver (I) oxide and base. The reaction vessel was then capped and secured in an ice bath at 0°–5° C. and allowed to equilibrate for 15 minutes. When the solution had reached between 0°–5° C., alkyl halide was added. The vessel was tightly capped and allowed to stir for the amount of time indicated in the table. During this time the reaction temperature was allowed in some cases to come up to room temperature. The flask was then removed from its temperature bath and the solution quickly filtered through a plug of celite to remove excess silver (I) oxide. The filtrate was then evaporated to a minimum and the residue or syrup quickly redissolved in ethyl acetate and extracted with a 5% aqueous solution of sodium iodide buffered with 1M sodium citrate pH 6.0. The pH of the aqueous layer was monitored and maintained at 6.0 to 8.0 by addition of 1M aqueous sodium citrate solution. The heterogeneous solution was filtered again through a celite plug and the extraction continued. The sodium iodide extraction procedure was repeated on the organic layer until no more silver iodide precipitated. The remaining organic layer was dried over sodium sulfate, filtered and evaporated to a foam. The crude product could be analyzed by reversed phase HPLC (See Tables 1–3). The product was then purified by silica gel chromatography (hexane:ethyl acetate:methanol) to yield pure product.

Example 4

Synthesis of 2'-O-methyl-5'-O-dimethoxytrityl-uridine

To 2'-O-methyl-5'-O-dimethoxytrityl-$N^4$-t-butylphenoxyacetyl-cytidine (80 g, 0.107 mole; Biosearch, USA) was added methanol (200 mL) and the mixture was allowed to stir until completely dissolved. A condenser was attached and the stirring mixture was heated to facilitate dissolution. To the stirring solution was then added a 4M aqueous lithium hydroxide solution (800 mL) and the reaction was brought to reflux. About every hour, analysis of the reaction was performed by thin-layer chromatography. When complete (6–8 hrs), the heat was removed and the solution cooled to room temperature. The solution was neutralized with ammonium chloride to pH 7–8 and then the product was extracted into two volumes of ethyl acetate. The ethyl acetate layers were combined and dried over sodium sulfate. The solution was then filtered and evaporated to yield 58 g of crude product which by $^1$H-NMR consisted of 93% 2'-O-methyl-5'-dimethoxytrityl-uridine and 6% of 3'-O-methyl-5'-O-dimethoxytrityl-uridine. Final purification was achieved by silica gel chromatography using a 0–1% methanol gradient in dichloromethane. Fractions were analyzed by $^1$H-NMR to determine content of 3'-O-methyl-5'-O-dimethoxytrityl-uridine. Pure product fractions were pooled and evaporated. Yield 36.2 g (60%) $^1$H-NMR (CDCl$_3$) δ9.22 (1H, br s), 8.06 (1H, d), 7.45–7.15 (9H, m), 6.82 (4H, d), 5.98 (1H, d), 5.27 (1H, d), 4.48 (1H, q), 4.46 (1H, m), 3.98 (1h, dt), 3.81 (6H, s), 3.62 (3H, s) 3.56 (3H, m), 2.64 (1H, d).

Example 5

Synthesis of 2'-O-methyl-5'-O-dimethoxytrityl-uridine-3'-O-(O-2-cyanoethyl, N,N-diisopropyl) phosphoramidite To a 1 L flask containing 100 g dried (co-evaporate from dry toluene), 2'-O-methyl-5'-O-dimethoxytrityl-uridine was added 500 mL of dry THF (Fluka, P/N 87371). The stirring solution was sealed tightly with a rubber septum and purged with a stream of argon. To the vigorously stirring solution was added 76 mL (2.5 eq.) of dry diisopropylethylamine (Aldrich, P/N D12,580-6) and 54 mL (1.3 eq.) of O-β-cyanoethyl, N,N-diisopropyl chlorophosphine (Biosearch, P/N JGBY70000) using a dry, argon purged 60 mL glass syringe with stainless steel needle. The reaction was then allowed to stir under argon. The reaction was analyzed for completion by TLC in 100% ethyl acetate. When complete (2 hrs), the reaction was transferred to a rotavap and evaporated under reduced pressure to 200 mL (approximate). No heat was applied to the pot during evaporation. The solution was then cooled to 0° C. and the white salts filtered off. The precipitate was washed with 100 mL ice cold, argon purged, ethyl acetate. All ethyl acetate layers were combined and the solution was then transferred to a 2 L separatory funnel. To the funnel was also added 400 mL ice cold, argon purged, ethyl acetate and 300 mL ice cold, argon purged, aqueous 5% (50 g/L) sodium bicarbonate. The product was extracted into the organic layer after thorough mixing and venting. The ethyl acetate layer was then dried for 30 minutes over 20 g sodium sulfate in a sealed flask. The solution was then filtered and washed once with cold ethyl acetate. The solution was then evaporated under reduced pressure while applying very little heat. The off white foam was dried overnight under high vacuum at room temperature. The final product was isolated by silica gel chromatography using a gradient of 30–100% ethyl acetate in hexane containing 0.5% pyridine. Yield 81 grams (80%).

Because of the chirality of the phosphorous the product contains two diastereomers.

$^{31}$P NMR (CDCl$_3$) δ151.47 (1P, s), 150.95 (1P, s)

$^1$H NMR (CDCl$_3$) δ8.09 (1H, d), 7.97 (1H, d), 7.45–7.18 (18H, m), 6.90–6.78 (8H, m), 6.06–5.95 (2H, dd), 5.25 (2H, dd), 4.63 (1H, m), 4.47 (1H, m), 4.23 (2H, m), 3.91 (4H, m), 3.81 (12H, s), 3.65 (4H, m), 3.60 (6H, s), 3.58–3.40 (6H, m), 2.59 (2H, t), 2.42 (2H, t), 1.29 (12H, d), 1.02 (6H, d).

Example 6

General Deamination Procedure

Reagent equivalents can be deduced from data in Tables 4. If the table so indicates, the reagent was not added. To the partially protected 2'-O-derivatized cytosine ribonucleoside was added methanol (2.5 mL/gram) and the mixture was allowed to stir until completely dissolved. A condenser was attached and the stirring mixture was heated to facilitate dissolution. To the stirring solution was then added a 4M aqueous lithium hydroxide solution (4×the volume of methanol) and the reaction was brought to reflux. About every hour, analysis of the reaction was performed by thin-layer chromatography. When complete (see table), the heat was removed and the solution cooled to room temperature. The solution was then neutralized with ammonium chloride to pH 7–8 and then the product was extracted into two volumes of ethyl acetate. The ethyl acetate layers were combined and dried over sodium sulfate. The solution was then filtered and evaporated to yield crude product which was analyzed by $^1$H-NMR. Final purification was achieved by silica gel chromatography using a 0–1% methanol gradient in dichloromethane. Fractions were analyzed by $^1$H-NMR to determine content of 3'-O-derivatized uridine. Pure product fractions were pooled and evaporated.

It will be apparent to those skilled in the art that various modifications and variations can be made in the method of the present invention without departing from the spirit or scope of the invention. Thus, it is intended that the present invention cover the modifications and variations of this invention provided they come within the scope of the appended claims and their equivalents.

What is claimed is:

1. A method for derivatizing the 2'-hydroxyl group of a partially protected cytosine ribonucleoside having an unprotected 2' and 3'-hydroxyl group, the method comprising the step of:

reacting said partially protected cytosine ribonucleoside with at least one equivalent of metal salt catalyst, at least 1 equivalent of a hydrocarbon halide, and less than one equivalent of base under conditions sufficient to preferentially derivatize the 2'-hydroxyl group over the 3' hydroxyl group in a ratio of better than 65:35, respectively.

2. The method of claim 1 wherein the partially protected cytosine ribonucleoside comprises an acid labile 5'-hydroxyl group protecting group.

3. The method of claim 1 wherein the partially protected cytosine ribonucleoside comprises an ammonia labile C4 exocyclic amino group protecting group.

4. The method of claim 1 wherein the partially protected cytosine ribonucleoside comprises an acid labile 5'-hydroxyl group protecting group and an ammonia labile C4 exocyclic amino group protecting group.

5. The method of claim 1 wherein said partially protected cytosine ribonucleoside has the formula:

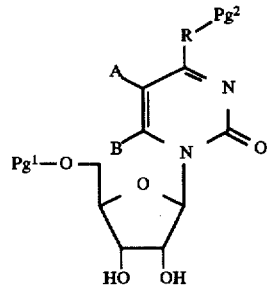

Formula 1 wherein R is NH or —N=.

6. The method of claim 5 wherein,

Pg¹ is an acid labile protecting group suitable for protecting the 5'-hydroxyl group from alkylation; Pg² is a ammonia labile protecting group suitable for protecting the C4 exocyclic amino group from alkylation; A and B are individually either hydrogen, methyl, ethyl, propyl, isopropyl, butyl, t-butyl, fluorine, chlorine, bromine or iodine.

7. The method of claim 5 wherein,

Pg¹ is a protecting group selected from the group consisting of triphenylmethyl, 4-methoxytriphenylmethyl, 4,4'-dimethoxytriphenylmethyl, 4,4',4"-trimethoxytriphenylmethyl, 9-phenylxanthene-9-yl (pixyl), t-butyldimethylsilyl, triisopropylsilyl, triethylsilyl, ethyldiisopropylsilyl and ethyldiphenylsilyl;

Pg² is a protecting group selected from the group consisting of acetyl, isobutyryl, trimethylacetyl, benzoyl, phenoxyacetyl, and t-butylphenoxyacetyl and R=NH or Pg² is selected from the group consisting of N,N-dialkylaminomethynyls and R=—N=, A and B are individually either hydrogen, methyl, ethyl, propyl, isopropyl, butyl, t-butyl, fluorine, chlorine, bromine or idodine.

8. The method of claim 5 wherein said partially protected cytosine ribonucleoside has the formula:

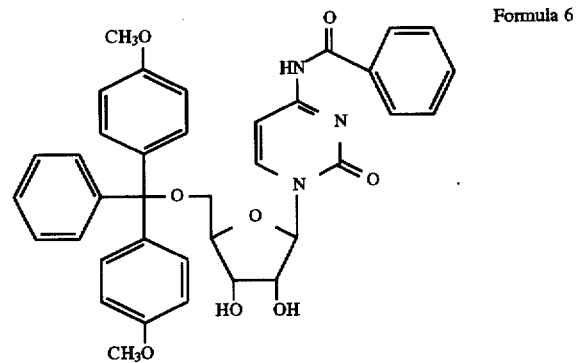

Formula 6

9. The method of claim 5 wherein said partially protected cytosine ribonucleoside has the formula:

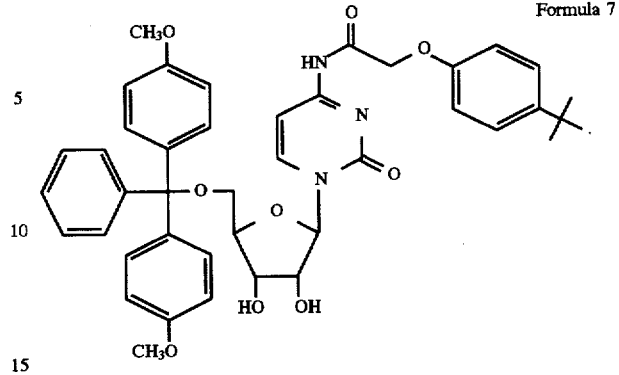

Formula 7

10. The method of claim 1 wherein the metal salt catalyst is selected from the group consisting of silver oxide, tin oxide, silver chloride, tin chloride and silver triflate.

11. The method of claim 1 wherein the metal salt catalyst is silver (I) oxide.

12. The method of claim 1 wherein the hydrocarbon halide is a straight chain or branched alkyl halide of the formula $C_nH_{2n+1}X$ wherein n is an integer from 1 to 20 and X is a halogen atom.

13. The method of claim 12 wherein the alkyl halide is selected from the group consisting of methyl iodide, ethyl iodide, propyl iodide and pentyl iodide.

14. The method of claim 1 wherein the hydrocarbon halide is a straight chain or branched alkenyl halide of the formula $C_nH_{2n-1}X$ wherein n is an integer from 1 to 20 and X is a halogen atom.

15. The method of claim 14 wherein the alkenyl halide is allyl iodide.

16. The method of claim 1 wherein the hydrocarbon halide is selected from the group consisting of dimethylallyl halide, cinnamyl halide and 4-nitrocinnamyl halide.

17. The method of claim 1 wherein the base is selected from the group consisting of N,N-dimethylamino pyridine, N,N-diisopropylethylamine, quinoline and 2-tert Butylimino-2-diethylamino-1,3-dimethylperhydro-1,3,2-diazaphosphorine.

18. The method of claim 1 wherein the base is a substituted pyridine.

19. The method of claim 18 wherein the substituted pyridine is 2,6-lutidine or sym-collidine.

20. The method of claim 1 wherein the base is pyridine.

* * * * *